(12) United States Patent
Fabrikant et al.

(10) Patent No.: US 7,301,649 B2
(45) Date of Patent: *Nov. 27, 2007

(54) SYSTEM FOR SCATTEROMETRIC MEASUREMENTS AND APPLICATIONS

(75) Inventors: Anatoly Fabrikant, Fremont, CA (US); Guoheng Zhao, Milipitas, CA (US); Daniel C. Wack, Los Altos, CA (US); Mehrdad Nikoonahad, Menlo Park, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/192,056

(22) Filed: Jul. 27, 2005

(65) Prior Publication Data
US 2005/0274901 A1    Dec. 15, 2005

Related U.S. Application Data

(62) Division of application No. 09/671,715, filed on Sep. 27, 2000.

(51) Int. Cl.
*G01B 11/34* (2006.01)
*G01J 4/00* (2006.01)

(52) U.S. Cl. .................. 356/625; 356/630; 356/369; 356/237.5; 250/225

(58) Field of Classification Search ........ 356/364–369, 356/601, 625, 636, 445
See application file for complete search history.

(56) References Cited

U.S. PATENT DOCUMENTS 5,608,526 A    3/1997  Piwonka-Corle et al.

(Continued)

FOREIGN PATENT DOCUMENTS

WO    WO99/45340    9/1999

OTHER PUBLICATIONS

U.S. Appl. No. 60/224,451, filed Aug. 10, 2000, to Stanke et al., cited in USP 6,768,967, 28 pgs.

(Continued)

*Primary Examiner*—Layla G. Lauchman
(74) *Attorney, Agent, or Firm*—Davis Wright Tremaine LLP

(57) ABSTRACT

Instead of constructing a full multi-dimensional look-up-table as a model to find the critical dimension or other parameters in scatterometry, regression or other optimized estimation methods are employed starting from a "best guess" value of the parameter. Eigenvalues of models that are precalculated may be stored and reused later for other structures having certain common characteristics to save time. The scatterometric data that is used to find the value of the one or more parameter can be limited to those at wavelengths that are less sensitive to the underlying film characteristics. A model for a three-dimensional grating may be constructed by slicing a representative structure into a stack of slabs and creating an array of rectangular blocks to approximate each slab. One dimensional boundary problems may be solved for each block which are then matched to find a two-dimensional solution for the slab. A three-dimensional solution can then be constructed from the two-dimensional solutions for the slabs to yield the diffraction efficiencies of the three-dimensional grating. This model can then be used for finding the one or more parameters of the diffracting structure in scatterometry. Line roughness of a surface can be measured by directing a polarized incident beam in an incident plane normal to the line grating and measuring the cross-polarization coefficient. The value of the one or more parameters may then be supplied to a stepper or etcher to adjust a lithographic or etching process.

25 Claims, 10 Drawing Sheets

U.S. PATENT DOCUMENTS

| | | | |
|---|---|---|---|
| 5,739,909 | A | 4/1998 | Blayo et al. |
| 5,751,427 | A | 5/1998 | De Groot |
| 5,900,939 | A | 5/1999 | Aspnes et al. |
| 5,963,329 | A | 10/1999 | Conrad et al. |
| 5,978,074 | A | 11/1999 | Opsal et al. |
| 6,097,488 | A | 8/2000 | Grek et al. |
| 6,268,916 | B1 | 7/2001 | Lee et al. |
| 6,483,580 | B1 | 11/2002 | Xu et al. |
| 6,657,736 | B1 | 12/2003 | Finarov et al. |
| 6,728,663 | B2 | 4/2004 | Krukar et al. |
| 6,768,967 | B2 | 7/2004 | Johnson et al. |
| 6,900,892 | B2 | 5/2005 | Shchegrov et al. |
| 2004/0107066 | A1 | 6/2004 | Poola et al. |

OTHER PUBLICATIONS

International Search Report from corresponding PCT Appln. PCT/US01/30063, dated Dec. 21, 2001, 4 pages.

International Preliminary Examination Report from corresponding PCT Appln. PCT/US01/30063, dated Jan. 16, 2003, 6 pages.

Written Opinion from corresponding PCT Appln. PCT/US01/30063, dated Sep. 18, 2002, 5 pages.

International Application Pub. No. WO02/50501 A1, published with International Search Report on Jun. 27, 2002.

International Search Report for PCT application No. PCT/US01/49001 dated Apr. 18, 2002, 6 pages.

Patent Search conducted on Aug. 1, 2000, 53 pages.

Aspnes, D.E., "Effects of component optical activity in data reduction and calibration of rotating-analyzer ellipsometers", Journal of Optical Society of America, vol. 64, No. 6, Jun. 1974, pp. 812-819.

Azzam, R. M .A., "Ellipsometry", "Handbook of Optics, vol. 2, Devices, Measurements and Properties", Second Edition, Optical Society of America, McGraw Hill, Inc. 1995, 27 pages.

Blayo et al., "Ultraviolet-Visible Ellipsometry for Process Control During the Etching of Submicrometer Features" J. Opt. Soc. Am. A., vol. 12, No. 3, Mar. 1995, pp. 591-599.

Chipman, "Polarimetry", Handbook of Optics, vol. 2, Devices, Measurements and Properties, Second Edition, Optical Society of America, McGraw Hill, Inc. 1995, 37 pages.

Collins, R. W., "Automatic rotating element ellipsometers: Calibration, operation, and real-time applications" Rev. Sci Instrum. 61, (8), Aug. 1990, pp. 2029-2062.

Crandall and Chipman, "Polarization aberrations of crossed folding mirrors", *SPIE*, vol. 2537, pp. 83-93.

Li, "Formulation and Comparison of Two Recursive Matrix Algorithms for Modeling Layered Diffraction Gratings", J. Opt. Soc. Am. A/vol. 13, No. 5, May 1996, pp. 1024-1035.

Li, "Multilayer Modal Method for Diffraction Gratings of Arbitrary Profile, Depth, and Permittivity", J. Opt. Soc. Am. A/vol. 10, No. 12, Dec. 1993, pp. 2581-2591.

Moharam et al., "Formulation for Stable and Efficient Implementation of the Rigorous Coupled-Wave Analysis of Binary Gratings", J. Opt. Soc. Am. A./vol. 12, No. 5, May 1995, pp. 1068-1076.

Moharam et al., "Rigorous coupled-wave analysis of planar-grating diffraction", SPIE: vol. 71, No. 7, Jul. 1981, pp. 811-818.

Moharam, "Coupled-Wave Analysis of Two-Dimensional Dielectric Gratings", SPIE: vol. 883, Holographic Optics: Design and Applications (1988), pp. 8-11.

Schramm et al., "Algorithm Implementation and Techniques for Providing More Reliable Overlay Measurements and Better Tracking of the Shallow Trench Isolation (STI) Process", SPIE: Conference on Metrology, Inspection, and Process Control of Microlithography XIII, Mar. 1999, pp. 116-122.

Yasuda and Aspnes "Optical-standard surfaces of single-crystal silicon for calibrating ellipsometers and reflectometers", Applied Optics, vol. 33, No. 31, Nov. 1994, Optical Society of America, pp. 7435-7437.

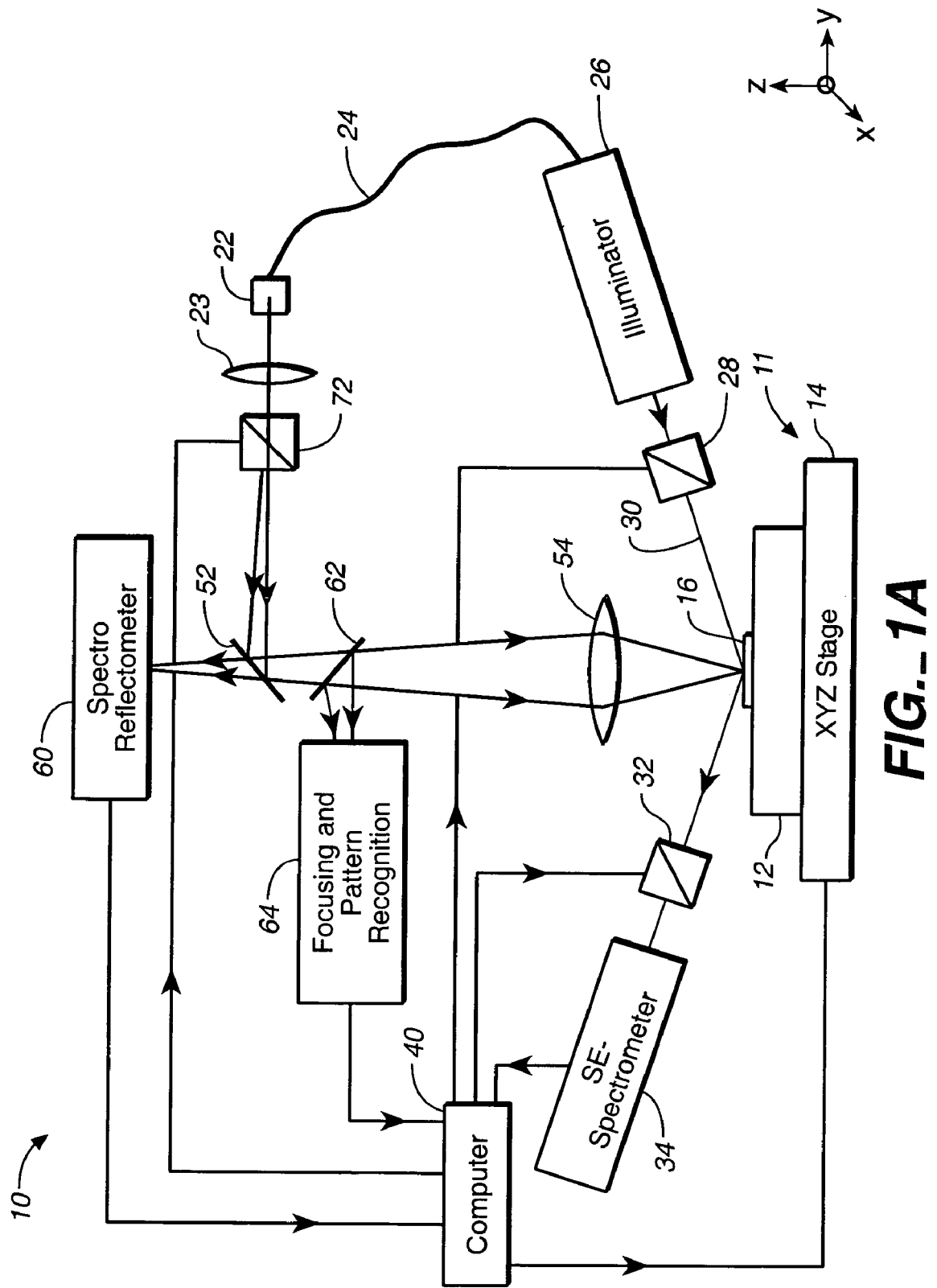
FIG._1A

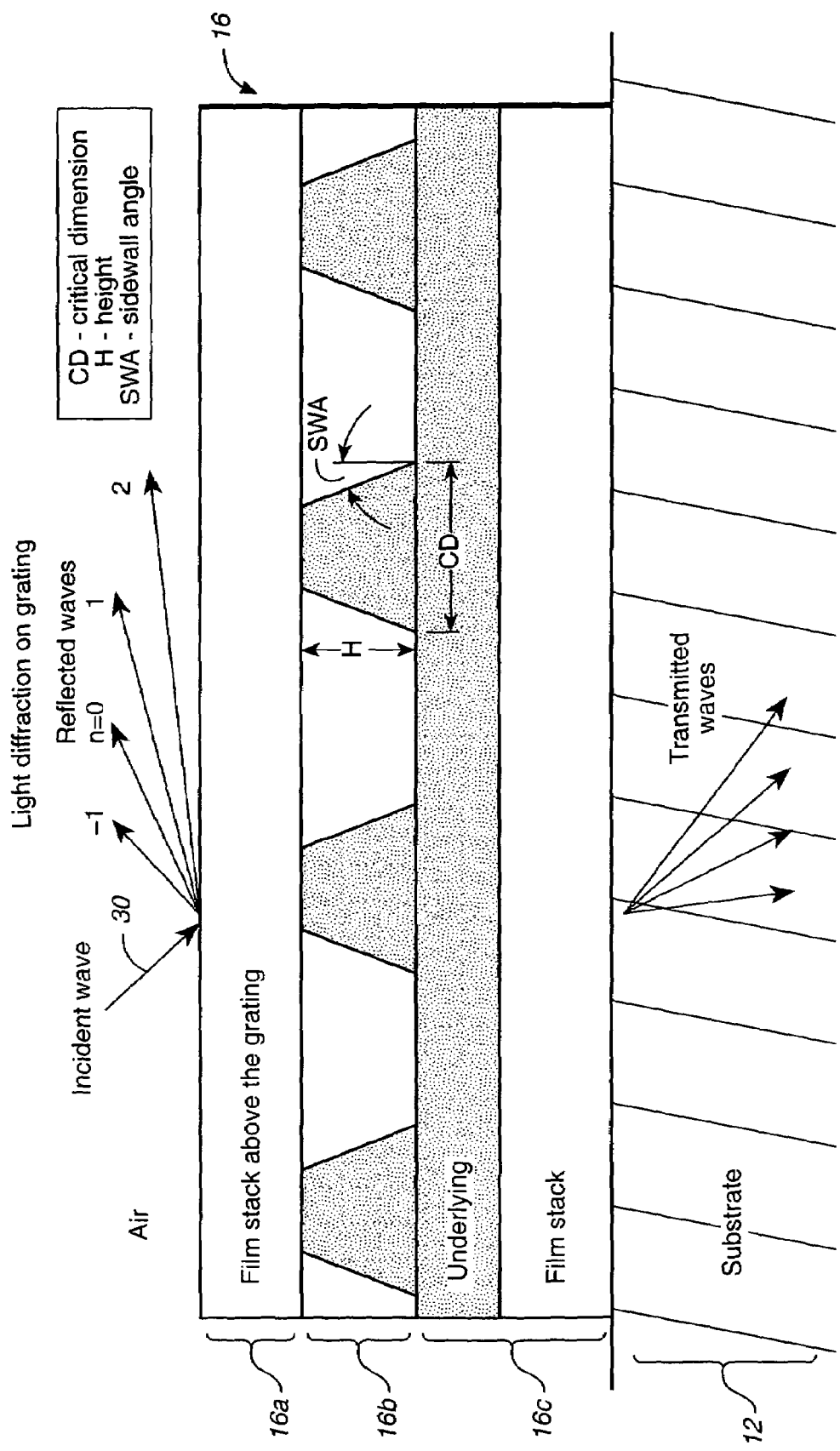
FIG._1B

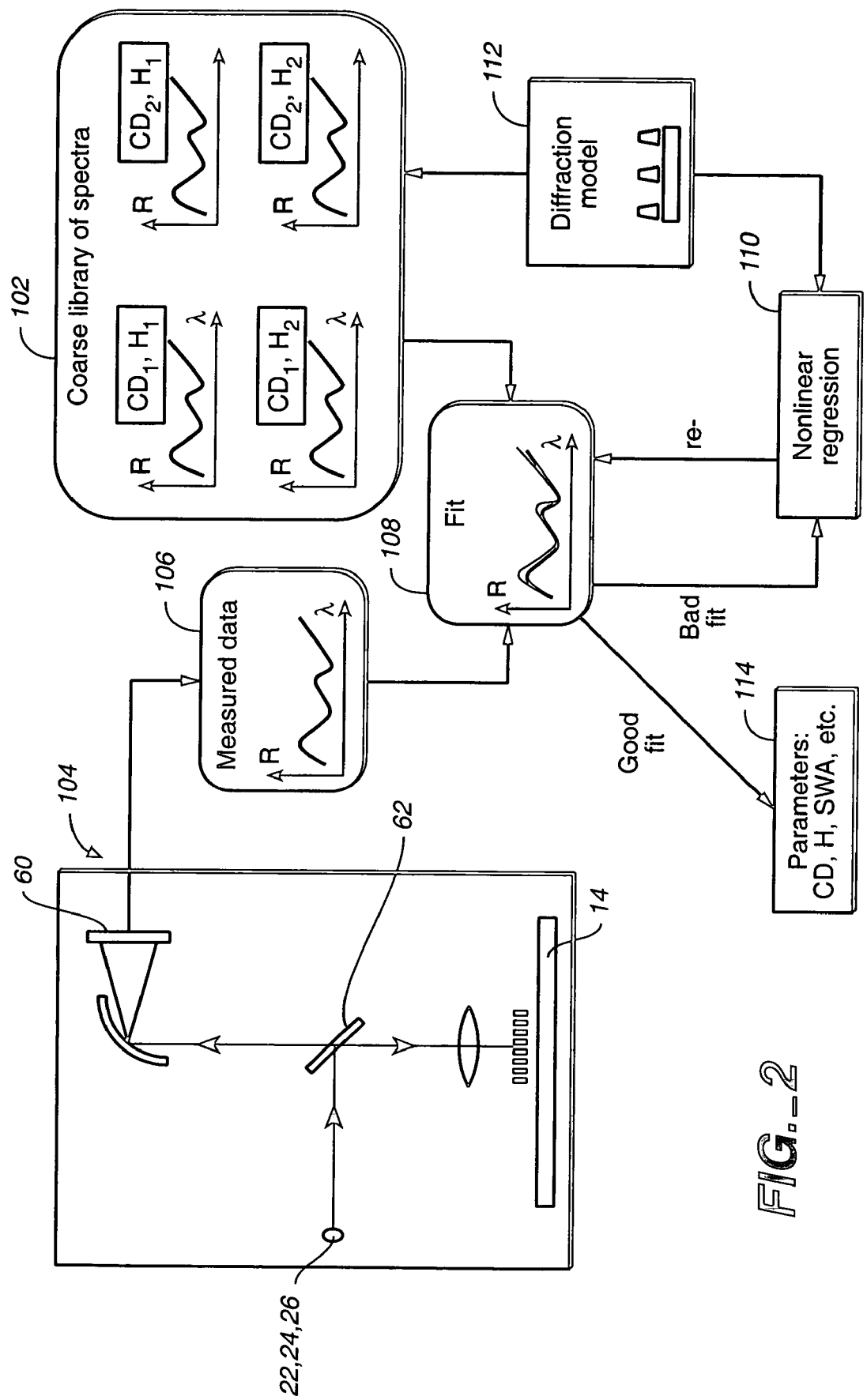
FIG._2

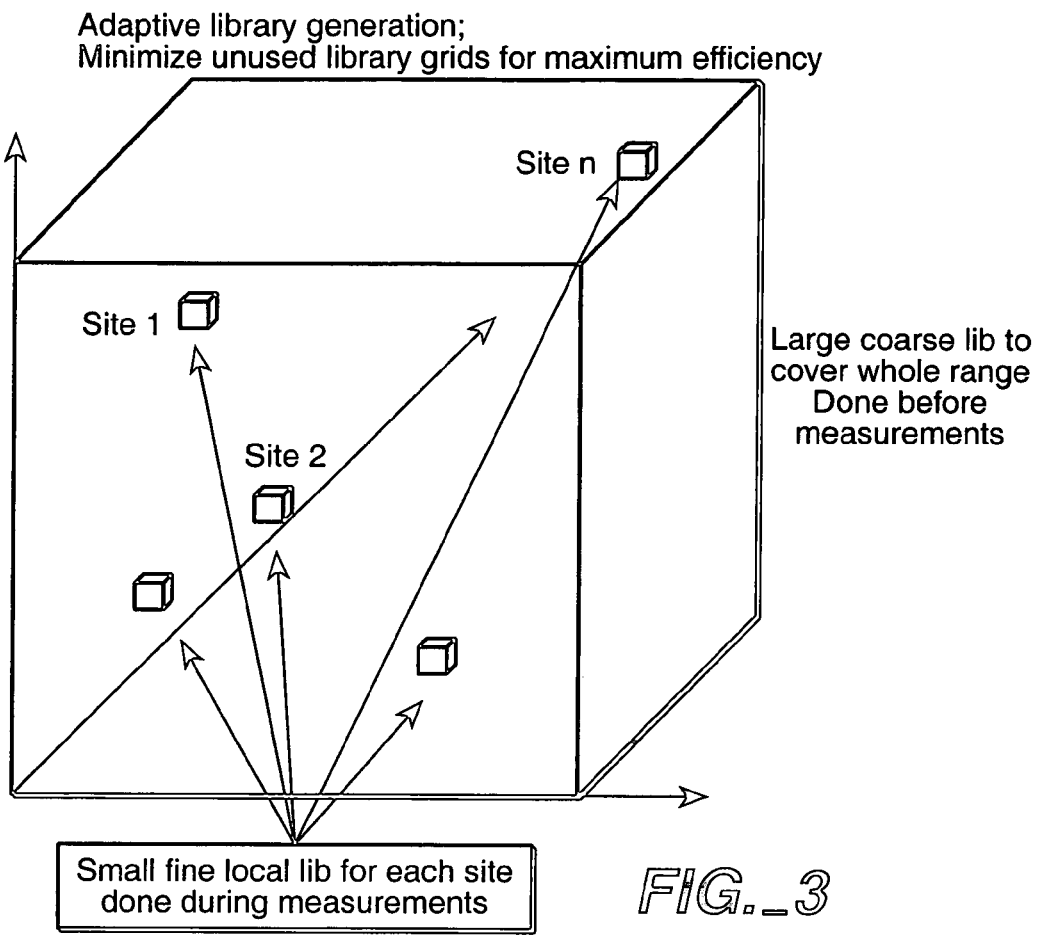
FIG._3
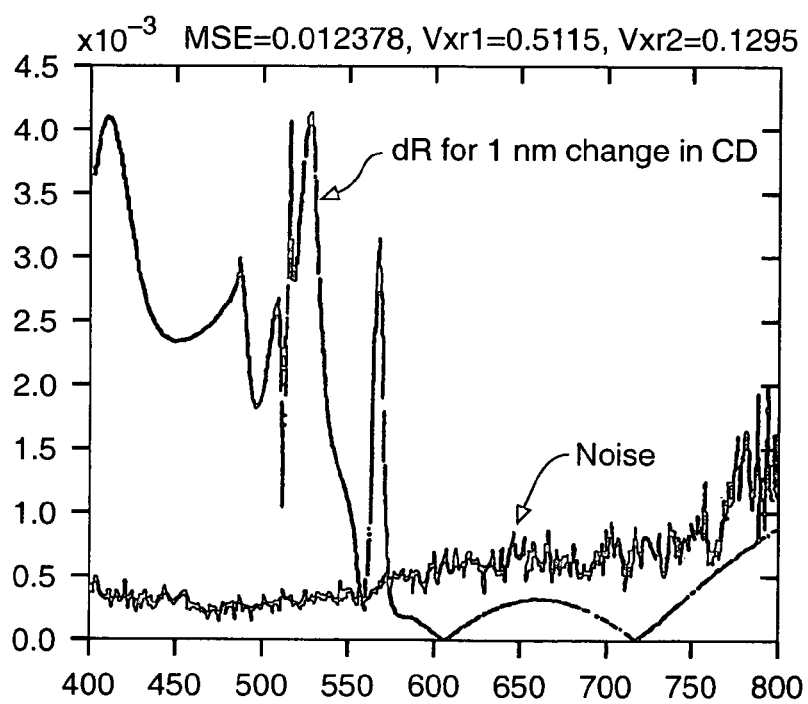
FIG._4

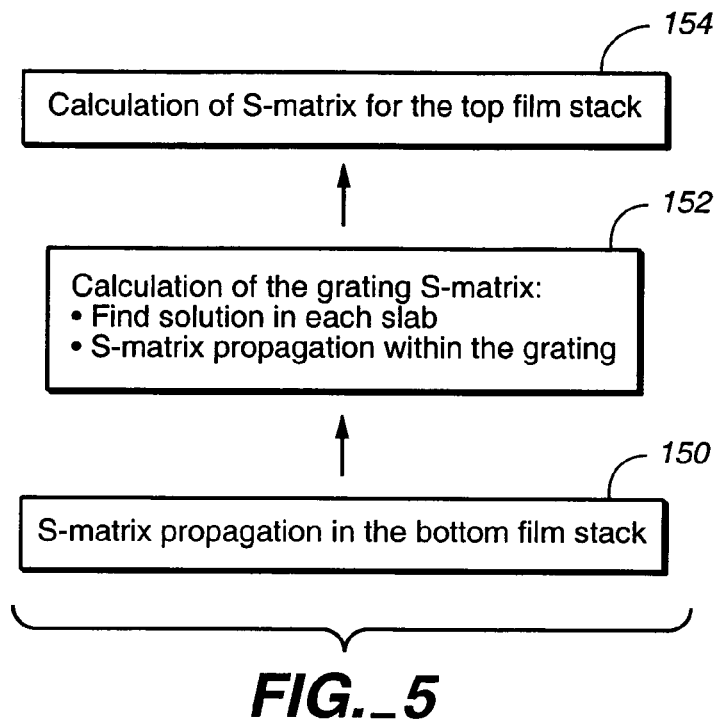
FIG._5
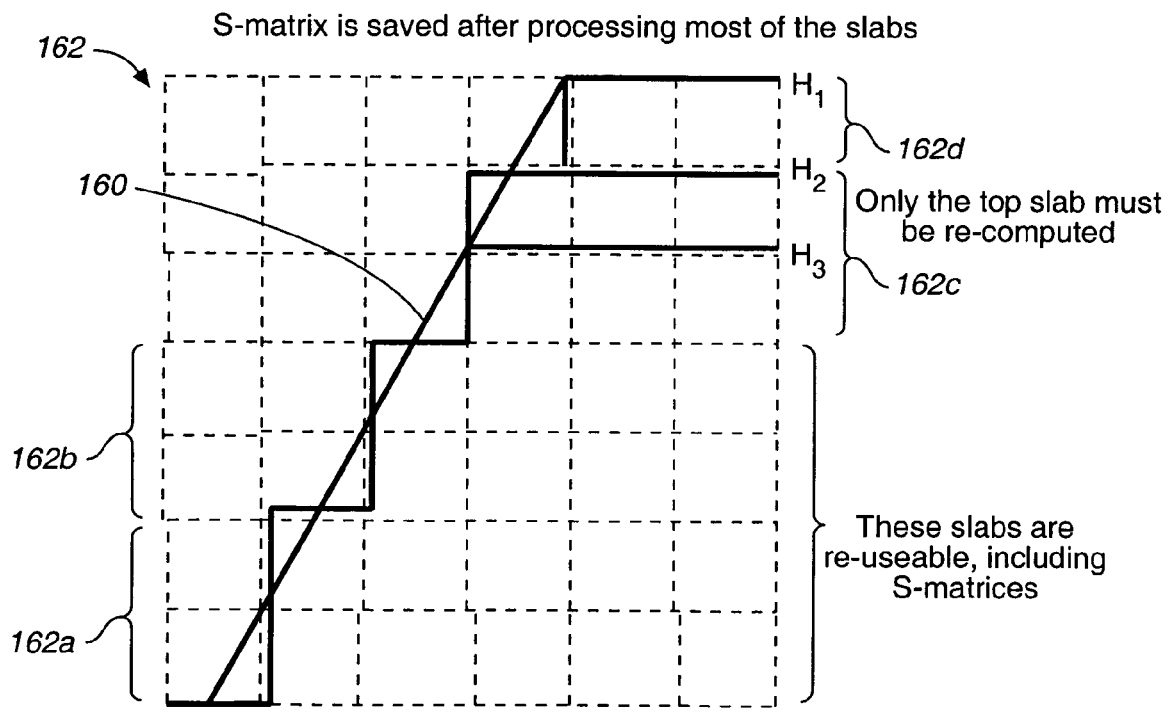
FIG._6

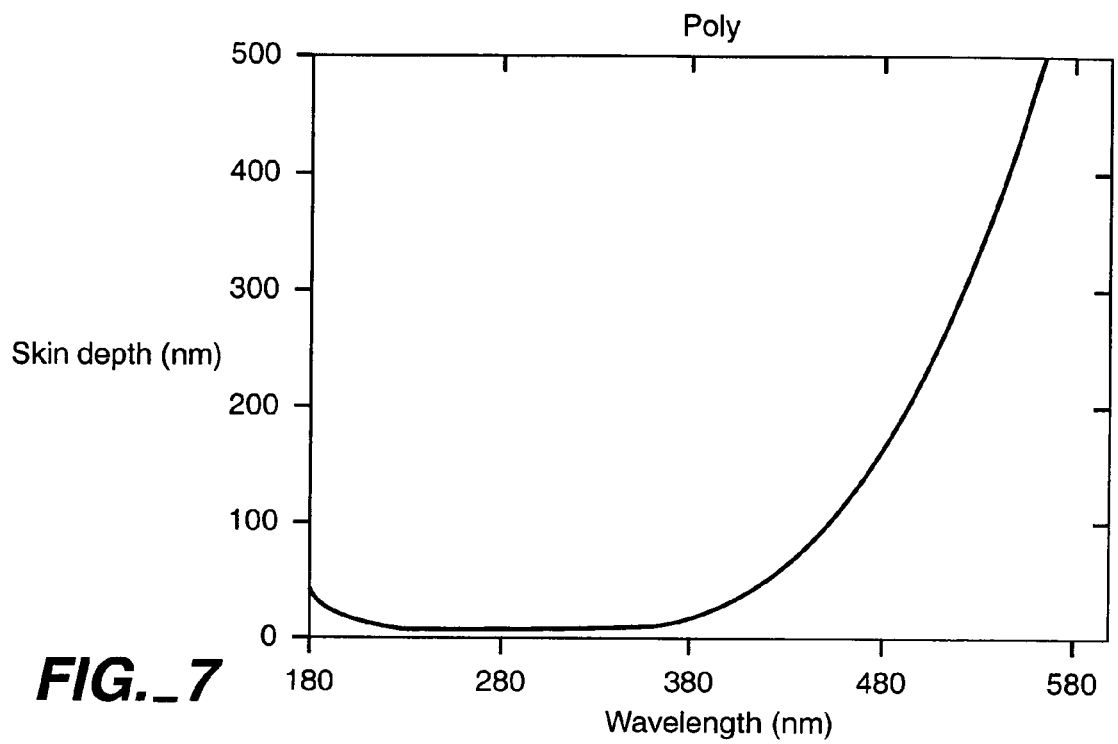
FIG._7
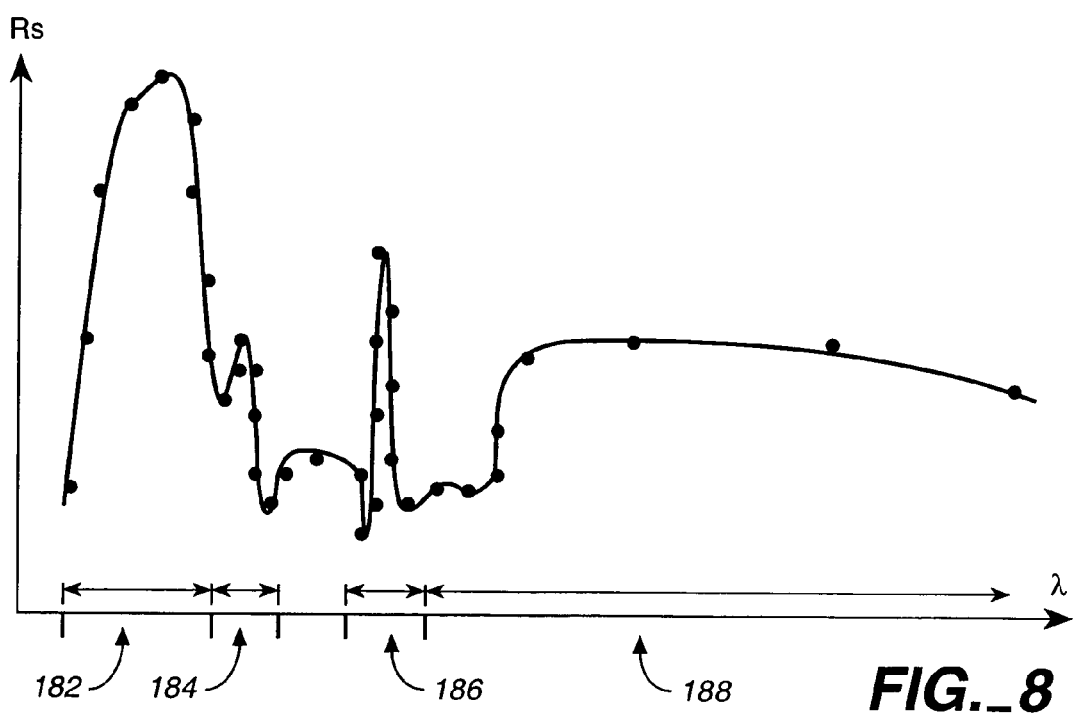
FIG._8

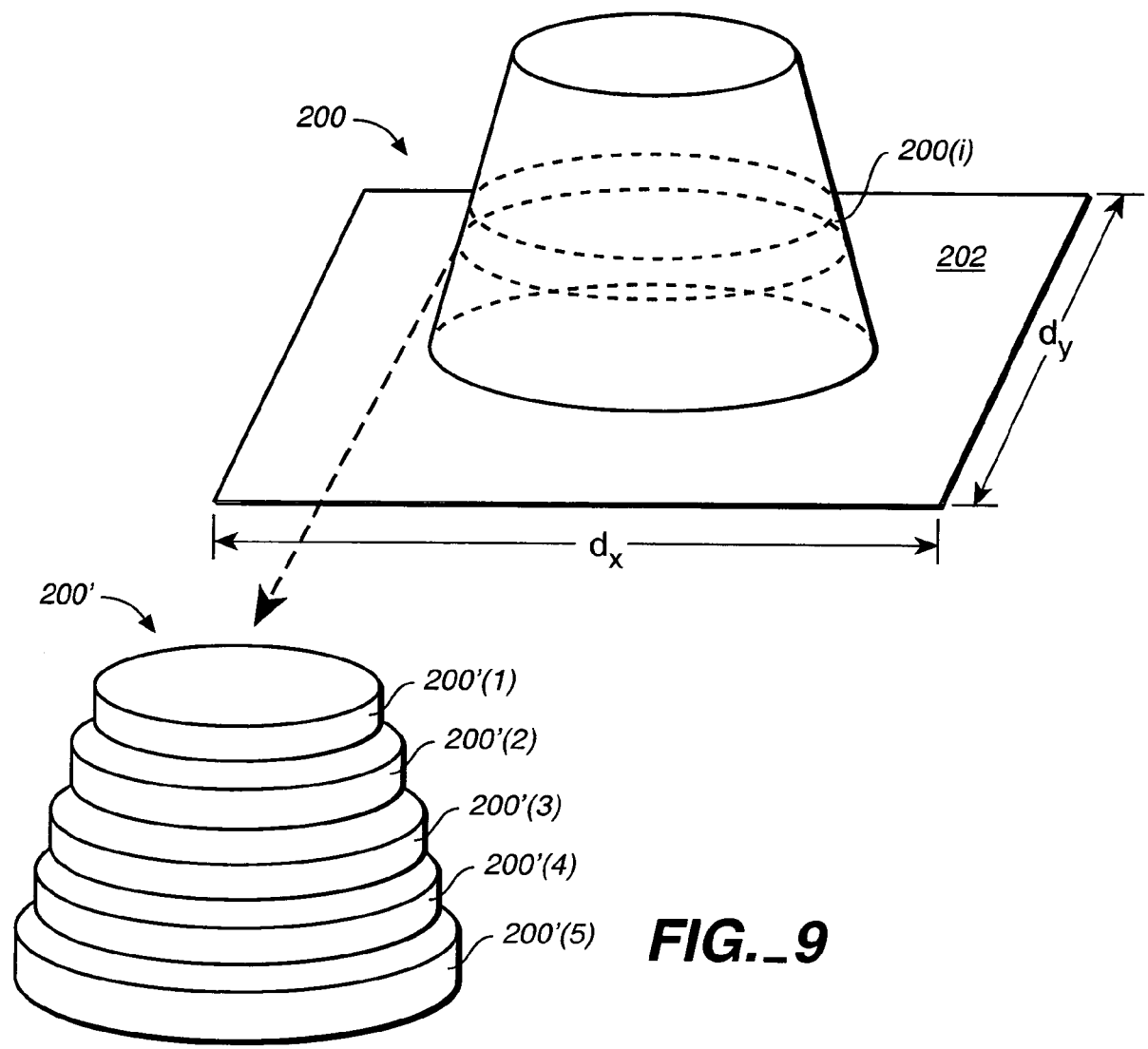
FIG._9

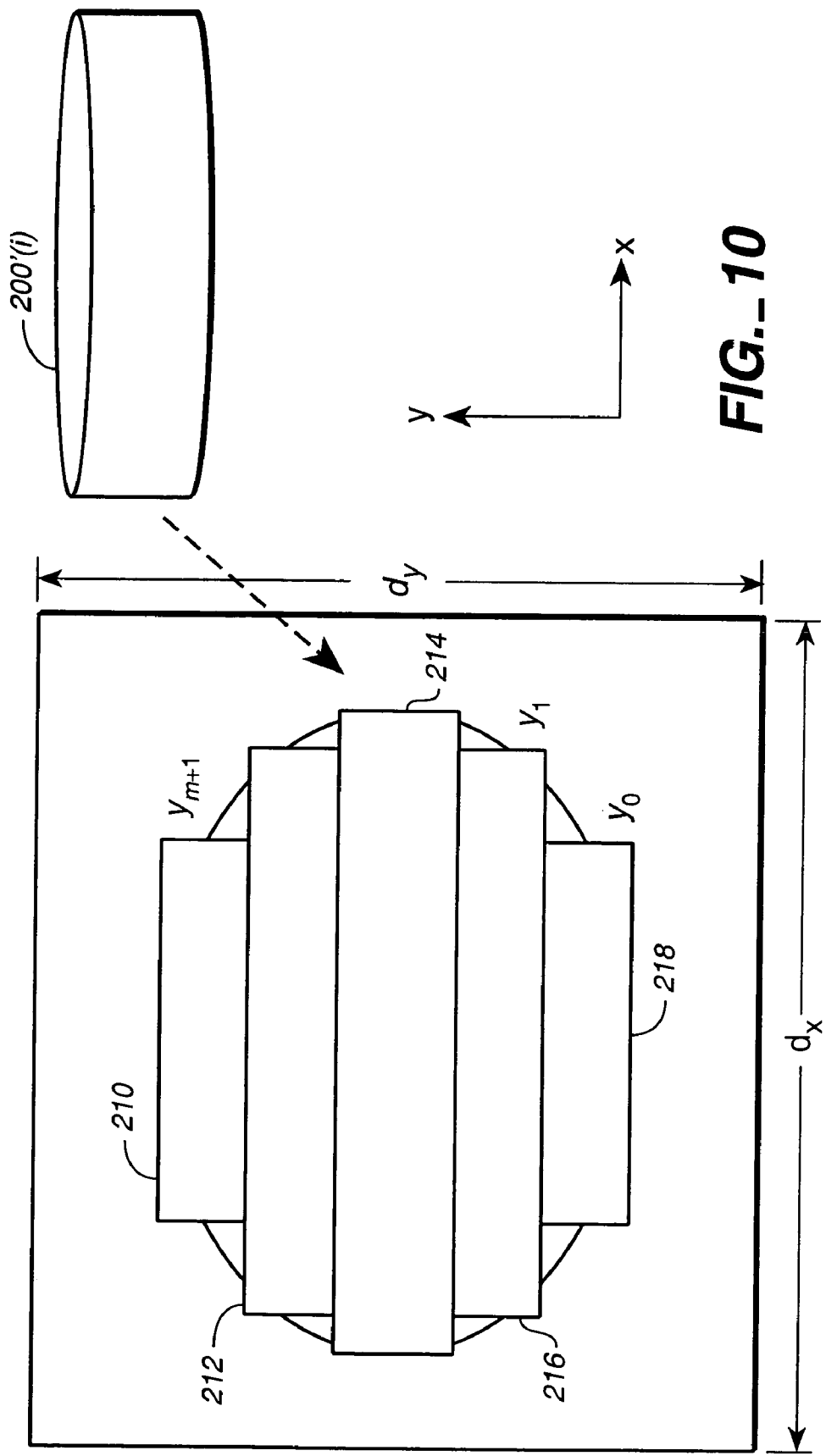

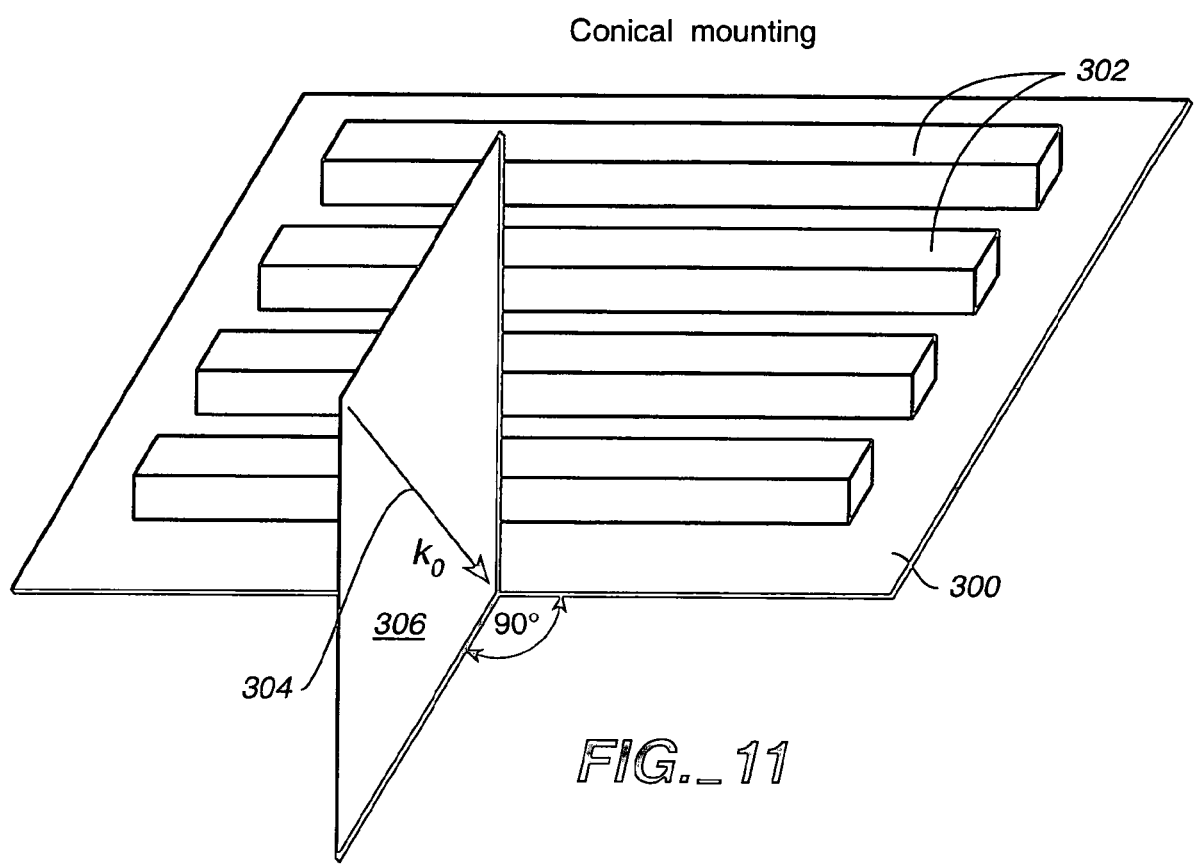
FIG._11

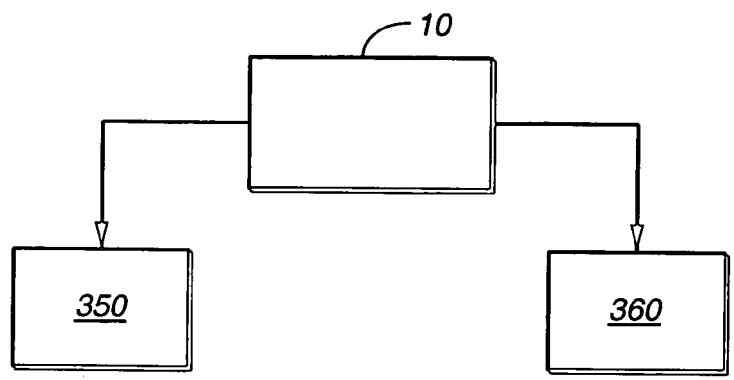
FIG._12
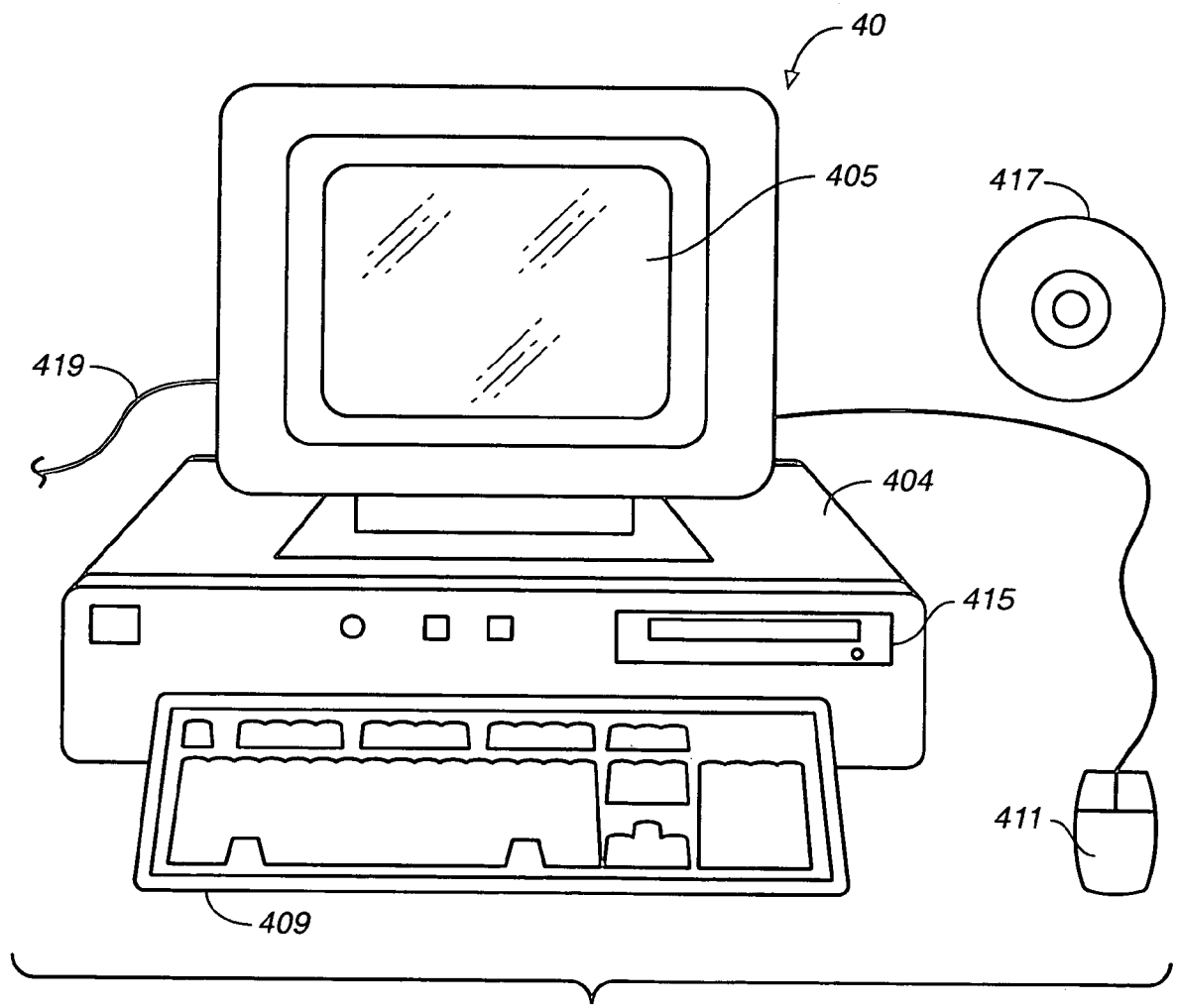
FIG._13

SYSTEM FOR SCATTEROMETRIC MEASUREMENTS AND APPLICATIONS

CROSS-REFERENCE TO RELATED APPLICATIONS

This application is a divisional of application Ser. No. 09/671,715, filed Sep. 27, 2000, which application is incorporated herein in its entirety by this reference.

BACKGROUND OF THE INVENTION

This invention relates in general to scatterometers and in particular, to spectroscopic scatterometric systems and methods employing models for measuring parameters of a diffracting structure as well as related applications to sample processing.

As the integration and speed of microelectronic devices increase, circuit structures continue to shrink in dimension size and to improve in terms of profile edge sharpness. The state-of-the-art devices require a considerable number of process steps. It is becoming increasingly important to have an accurate measurement of submicron linewidth and quantitative description of the profile of the etched structures on a pattern wafer at each process step. Furthermore, there is a growing need for wafer process monitoring and close-loop control such as focus-exposure control in photolithography.

Diffraction-based analysis techniques such as scatterometry are especially well suited for microelectronics metrology applications because they are nondestructive, sufficiently accurate, repeatable, rapid, simple and inexpensive relative to critical dimension-scanning electron microscopy (CD-SEM).

Scatterometry is the angle-resolved measurement and characterization of light scattered from a structure. For structures that are periodic, incident light is scattered or diffracted into different orders. The angular location $\theta_r$ of the $m^{th}$ diffraction order with respect to the angle of incidence $\theta_i$ is specified by the grating equation:

$$\sin\theta_i + \sin\theta_r = m\frac{\lambda}{d} \quad (1)$$

where $\lambda$ is the wavelength of incident light and d the period of the diffracting structure. Spectral scatterometry performs the above measurement using a variety of transmitted light that can be used for measurement of the grating parameters.

The diffracted light pattern or spectrum from a structure can be used as a "fingerprint" r "signature" for identifying the dimensions of the structure itself. In addition to period, more specific dimensions, such as width or critical dimension (CD), step height (H), and the shape of the line, and angle of the side-walls (SWA), or other variables referred to below as parameters of the structure, can also be measured by analyzing the scatter pattern.

In scatterometry, a diffraction model of the diffracting structure or grating is first constructed. Different grating parameters outlined above are parameterized and the parameter space is defined by allowing each parameter to vary over a certain range. A look-up-table is then constructed offline prior to measurements. The look-up-tables, also-called libraries, are multi-dimensional with the parameters such as CD, height and wall angle as the variable of each dimension. The tables contain typically, a collection of spectra where each spectrum is a plot of a measured diffraction reflectance or transmittance versus wavelength or illumination angle corresponding to a particular set of values of the parameters. After the sample spectrum is measured, it is compared to all the spectra in the look-up-table to find the best match and the value or values of the one or more parameters are then determined by the values at which the best match is found.

The look-up-tables are multi-dimensional and need to cover a number of parameters extending over different ranges. The end result is a multi-dimensional sampling grid with each point on the grid being a spectrum that contains hundreds of data points. Such tables are extremely time consuming to calculate and difficult to refine. If any parameter during real time measurement falls outside the sampling grid, or any dependent variables are different from what have been used for constructing the look-up-table, then the tables become useless and have to be reconstructed, which may take days. This drawback significantly reduces the value of integrated CD measurement systems, of which the main goal is to reduce the time delay from process to metrology results.

It is, therefore, desirable to provide an improved technique for deriving the important parameters of the diffracting structure from the measured data.

SUMMARY OF THE INVENTION

As noted above, the multi-dimensional look-up-table used in conventional scatterometry is extremely time consuming to calculate and difficult to refine. This invention is based on the recognition that processing delays can be much reduced by making use of knowledge of the diffraction structure to be measured. Thus, if the approximate values or ranges of values of the parameters are known, there is no need to employ a full sized look-up-table which contains all the data points over a full or maximum possible ranges of values for the parameters. In such event, one could make the "best guess" of the values of the parameters as a start and perform an optimal estimation process within a neighborhood of the "best guess" using measured data from the diffracting structure. Thus, this method involves computing only for more limited ranges of values for the parameters containing the initial set of guessed values of the parameters, which ranges of values may be smaller than those in the conventional method using a look-up-table containing data points over all possible values of the parameters.

Preferably, the optimized estimation employs non-linear regression or simulated annealing. In one embodiment, the initial set of guessed values is found as follows. First a coarse library of sets of data related to the diffraction at different wavelengths is constructed where the sets of data are generated assuming corresponding sets of values of the parameters covering the maximum possible or relatively large ranges of values. The diffracting structure may then be measured and the measured data is compared to the library to find the initial set of guessed values of parameters.

To speed up the process of matching measured data from the diffracting structure to those provided by the model which includes calculation of eigenvalues, the processing can be simplified and made faster by storing the eigenvalues so that the eigenvalues will not have to be recalculated every time matching is performed for different diffraction structures. The eigenvalues are then used to obtain the value of one or more parameters of a diffracting structure from measured data from the structure. In another embodiment, a look-up-table of the eigenvalues may also be pre-computed so that any eigenvalue within the needed range may be calculated with interpolation from the eigenvalue look-uptable. This will make the calculation of eigenvalues easier, faster, and more reliable, which improves the most time consuming and least robust part of modelling.

The diffracting structure measured frequently sits underneath and/or over a stack of one or more layers of material so that when electromagnetic radiation is directed at the structure to perform measurements, the measurements will be affected by the effects of such layers on the measurements. Therefore, where measurement of the structure is carried out by directing a polychromatic beam of electromagnetic radiation and detecting corresponding data of a diffraction of the beam at a number of wavelengths, the wavelengths at which the data on the structure is measured may be chosen as a function of the properties of the one or more layers. In one example, the wavelengths are chosen so that the measurements are less affected by the properties of the one or more layers. In this manner, measurement of similar structures will be less affected by the different layers in their vicinity.

When measurement of the structure is carried out by means of a polychromatic beam of electromagnetic radiation and detection of corresponding data of the beam at a number of wavelengths, the measured data may change more significantly over one wavelength range than over another. Thus, to provide more accurate sampling representation of the spectra, the density of the data samples over the wavelengths may be chosen as a function of sensitivity of the data to changes in the one or more parameters over the different wavelengths.

To model a three-dimensional diffracting structure, a model of the structure may be provided by cutting a three-dimensional contour resembling a portion of the structure along planes parallel to a reference plane to obtain a pile of slabs. An array of rectangular blocks arranged along planes parallel to the reference plane may be formed to approximate each slab. An analysis such as Multimodal analysis may be performed for each of the arrays to find a one-dimensional solution and the solutions of adjacent blocks are matched to find a two-dimensional solution for the array. A three-dimensional solution for the contour may then be formed from the two-dimensional solutions of the arrays.

Where measurements according to any one or more of the above-described features are performed by directing a polychromatic beam of electromagnetic radiation at the diffracting structure and data is detected from the structure, preferably the data measured includes intensities or changes in polarization state of the diffraction of the radiation of the structure.

Line roughness in the form of slight variations in height forming grating line patterns may be present on some samples where the roughness may be the result of certain sample processing steps. A beam of radiation is directed towards the grating lines in an incident plane which is substantially perpendicular to the lines, where the radiation supplied is of a known polarization state. By measuring the change in polarization state caused by diffraction by the lines, a measure of the line roughness can be obtained. Preferably, the incident radiation is linearly polarized of S- or P-polarization and a cross-polarization coefficient may be measured from the diffracted radiation as an indication of line roughness.

Any one of the above-described techniques may be used to find the value(s) of one or more parameters of a diffracting structure, and such value may be supplied to a sample processing machine, such as a stepper and/or etcher to control the lithographic and/or etching process in order to compensate for any errors in one or more of the parameters that has been discovered. The stepper and/or etcher may form an integrated single tool with the system for finding the one or more parameters of a diffracting structure, or may be instruments separate from it.

Any of the techniques described above may be performed by means of software components loaded into a computer or any other information appliance or digital device. When so enabled, the computer, appliance or device may then perform the above-described techniques to assist the finding of value(s) of the one or more parameters using measured data from a diffracting structure. The software component may be loaded from a fixed media or accessed through a communication medium such as the internet or any other type of computer network.

BRIEF DESCRIPTION OF THE DRAWINGS

FIG. 1A is a schematic view of a spectroscopic scatterometer useful for illustrating the invention.

FIG. 1B is a cross-sectional view of a two-dimensional grating useful for illustrating the invention.

FIG. 2 is a flow diagram illustrating an optimization estimation method to illustrate one aspect of the invention.

FIG. 3 is a schematic view of a large course library and small local libraries useful for illustrating the invention.

FIG. 4 is a graphical plot of reflectance spectrum of a resist grating on silicon to illustrate the sensitivity of the spectrum to the critical dimension (CD) and system noise to illustrate the invention.

FIG. 5 is a flow chart illustrating a method for propagating S-matrices in a sample including a diffraction grating, a top film stack on the grating and a bottom film stack below the grating to illustrate the invention.

FIG. 6 is a schematic view of multi-slab model for approximating a portion of a grating useful for illustrating the invention.

FIG. 7 is a graphical plot of the skin depth of polysilicon at different wavelengths of light.

FIG. 8 is a graphical plot of a reflectance spectrum of a diffraction as a function of wavelength to illustrate the sensitivity of the spectrum over different wavelengths.

FIG. 9 is a flow diagram illustrating the construction of a model to approximate a portion of a three-dimensional diffracting structure for illustrating the invention.

FIG. 10 is a schematic view of an array of rectangular blocks for approximating an elliptical or circular cylinder in the model of FIG. 9.

FIG. 11 is a perspective view of a two-dimensional grating relative to a plane of incidence of a measurement beam to illustrate a method for measuring line roughness.

FIG. 12 is a schematic block diagram illustrating a wafer processing apparatus including a stepper and an etcher and a scatterometer where parameter information from a diffracting structure and/or associated structures from the scatterometer is used to control the manufacturing process in the stepper and/or etcher to illustrate the invention.

FIG. 13 is a block diagram showing a representative sample logic device in which aspects of the present invention may be embodied.

For simplicity in description, identical components are labeled by the same numerals in this application.

DETAILED DESCRIPTION OF THE SPECIFIC EMBODIMENTS

Even though much of the description below of algorithms and methods are described in terms of the reflected or transmitted intensities of the diffraction caused by the diffracting structure, it will be understood that the same techniques and algorithms may be used for data containing information concerning changes in the polarization state over different wavelengths (e.g. ellipsometric parameters and as functions of wavelength). For this reason, it may be advantageous to employ an instrument which is capable of measuring both the reflected or transmitted intensities of the diffraction caused by the structure as well as changes in polarization state caused by the diffraction of the structure. A suitable system is described below in reference to FIG. 1A.

FIG. 1A is a schematic view of a spectroscopic scatterometer system to illustrate the preferred embodiment of the invention. As shown in FIG. 1A, system 10 may be used to measure reflected or transmitted intensities or changes in polarization states of the diffraction. As shown in FIG. 1A, a semiconductor wafer 11 may comprise a silicon substrate 12, and a structure 16 thereon that may include a photoresist pattern on and/or over film stack(s), where the film(s) are at least partially light-transmissive and has a certain film thickness and refractive index (n and k, the real and imaginary components of the index).

An XYZ stage 14 is used for moving the wafer in the horizontal XY directions. Stage 14 may also be used to adjust the z height of the wafer 11. A broadband radiation source such as white light source 22 supplies light through a fiber optic cable 24 which randomizes the polarization and creates a uniform light source for illuminating the wafer. Preferably, source 22 supplies electromagnetic radiation having wavelengths in the range of at least 180 to 800 nm. Upon emerging from fiber 24, the radiation passes through an optical illuminator that may include an aperture and a focusing lens or mirror (not shown). The aperture causes the emerging light beam to image a small area of structure 16. The light emerging from illuminator 26 is polarized by a polarizer 28 to produce a polarized sampling beam 30 illuminating the structure 16.

The radiation originating from sampling beam 30 that is reflected by structure 16, passed through an analyzer 32 and to a spectrometer 34 to detect different spectral components of the reflected radiation, such as those in the spectrum of the radiation source 22, to obtain a signature of the structure. In one mode (spectrophotometry mode) of operation, the reflected intensities are then used in a manner described below to find the value(s) of one or more parameters of structure 16. The system 10 can also be modified by placing the spectrometer 34 on the side of structure 16 opposite to illumination beam 30 to measure the intensities of radiation transmitted through structure 16 instead for the same purpose. These reflected or transmitted intensity components are supplied to computer 40. Alternatively, the light reflected by the structure 16 is collected by lens 54, passes through the beam splitter 52 to a spectrometer 60. The spectral components at different wavelengths measured are detected and signals representing such components are supplied to computer 40. The light reflected by structure 16 may be supplied by source 22 through illuminator 26 as described above or through other optical components in another arrangement. Thus, in such arrangement, lens 23 collects and directs radiation from source 22 to a beam splitter 52, which reflects part of the incoming beam towards the focus lens 54 which focuses the radiation to structure 16. The light reflected by the structure 16 is collected by lens 54, passes through the beam splitter 52 to a spectrometer 60.

When the system 10 is operated in another mode (spectroscopic ellipsometry mode) used to measure the changes in polarization state caused by the diffraction by the structure, either the polarizer 28 or the analyzer 30 is rotated (to cause relative rotational motion between the polarizer and the analyzer) when spectrometer 34 is detecting the diffracted radiation from structure 16 at a plurality of wavelengths, such as those in the spectrum of the radiation source 22, where the rotation is controlled by computer 40 in a manner known to those skilled in the art. The diffracted intensities at different wavelengths detected are supplied to computer 40, which derives the changes in polarization state data at different wavelengths from the intensities in a manner known to those in the art. See for example U.S. Pat. No. 5,608,526, which is incorporated herein by reference.

FIG. 1B is a cross-sectional view of the structure 16 on substrate 12, which structure comprises a diffracting structure 16b situated between the film stack 16a above the structure and the film stack 16c underneath the structure and an incident electromagnetic beam 30 to illustrate the invention. Thus, the incident beam 30 of the electromagnetic radiation first encounters the interface between the air and the film stack 16a and interfaces that may be present within the stack. Next, the portion of the radiation from beam 30 that penetrates the film stack 16a is diffracted by the grating structure 16b. At least some of the radiation from beam 30 will reach the film stack 16c underneath the grating and be reflected by or transmitted through interfaces associated with stack 16c. The total light reflectance is affected both by the grating and by the film stacks above and/or below the grating. Multi-layer interference, caused by multiple reflections between the films and the grating, creates a complicated pattern in a reflectance spectrum, which can be used for measuring parameters of the structure. A part of radiation from beam 30 that is not reflected or diffracted as described above will be transmitted into the substrate 12. As shown in FIG. 1B, the grating 16b has a height of H, a critical dimension CD and a side wall angle (SWA) as indicated.

FIG. 2 is a flow diagram illustrating a method for finding the value of one or more parameters of the grating structure 16b to illustrate an embodiment of the invention. As noted above, in conventional methods parameter space is created by allowing each of the parameters such as CD, H, SWA to vary over a wide range of values, such as all possible values at the step sizes dictated by precision requirement for the parameter. The predicted diffracted intensities are then calculated based on each set of parameter values to construct a multi-dimensional look-up-table. The intensities of the diffraction at different wavelengths from structure 16b is then measured using a spectrophotometer, such as the one shown in FIG. 1A. The measured diffracted intensities are then matched against the spectra in the look-up-table to find a best match. As noted above, the construction of the look-up-table is time consuming and cumbersome, since it covers a large number of values for the parameters. The process of matching can also be time consuming in view of the size of the table.

According to one aspect of the invention, the value of the one or more parameters is found by means of an optimized estimation process instead of by means of the multi-dimensional look-up-table. Thus, if the approximate value(s) of the one or more parameters is known, such value may be used as the starting point for the optimized estimation process, or the "best guess" value(s) of the one or more parameters of the grating structure. Thus, a set of predicted intensity data of the diffraction at multiple wavelengths is calculated according to the "best guess" value(s) of the one or more parameters of the grating structure. An optimized estimation process is then performed within the neighborhood of the predicted set of intensity of data using the measured intensities to arrive at a second value(s) of the one or more parameters. In one embodiment, the optimized estimation process employs nonlinear regression or simulated annealing. The above-described process is much faster than the conventional process using a multi-dimensional look-up-table.

In some circumstances, the approximate value(s) of the one or more parameters may not be known beforehand. In such circumstances a coarse library of spectra may be constructed as follows. The values of the parameters are allowed to vary substantially over their maximum possible ranges and spectra of predicted diffraction intensities over multiple wavelengths are then calculated based on such values of the parameters, using a diffraction model 112. The measured diffraction intensities are then matched against the spectra in the coarse library to find a "best guess" spectra as the starting point of the binary sequential estimation process. Different from the conventional method, however, since the goal of constructing the coarse library is merely to find the starting point of the optimized estimation process, the resolution of the library can be coarse, since the accuracy of estimation does not depend solely upon the resolution of the library, different from the conventional method.

The above-described process is illustrated in FIG. 2. First a coarse library of spectra of diffracted intensities over multiple wavelengths is constructed, each spectra being calculated assuming a corresponding set of values of the one or more parameters such as CD, H, SWA and other parameters as shown in block 102. The diffraction intensities from the structure are then measured as shown in block 104. The measured data 106 is then matched against the spectra in the library 102 as shown in block 108 to find a best match. The best match is then used as the "best guess" and the starting point of the optimized estimation process, such as nonlinear regression (block 110). The nonlinear regression process is then performed by varying the values of the set of parameters within the neighborhood of the "best guess" initial set of values for the parameters using a diffraction model 112 to arrive at a second set of values (114) that is a better fit to the measured data then the "best guess." This process may need to be repeated for some applications to arrive at a good fit to the measured data. The value(s) of the one or more parameters corresponding to this second set then give the dimensions of the structure 16b.

In the process described above in reference to FIG. 2, the data that is predicted or measured comprise the diffracted intensities from the grating structure. Instead of predicting or measuring diffracted intensities, it is also possible to find the value(s) of the one or more parameters by means of measuring and predicting changes in polarization state instead. In such event, instead of measuring the diffracted intensities using spectroreflectometer 60 (or spectrometer 34 but without rotating polarizer 28 or analyzer 32), SE spectrometer 34 from FIG. 1A is used instead to measure the change in polarization state of the diffraction to arrive at measured data 106 in FIG. 2. The diffraction model 112 is then modified to generate spectra of predicted changes in polarization state over multiple wavelengths as functions of different sets of values of the one or more parameters to arrive at the coarse library 102.

For the method of finding the value(s) of the one or more parameters using change in polarization state data, analogous to the situation involving reflected or transmitted intensity data as indicated above, where the "best guess" in terms of changes in polarization state is known beforehand, there is no need to construct a coarse library of spectra 102 at all. One may then also omit the step of comparing the measured data to the spectra in the coarse library 102 to find the "best guess."

FIG. 3 is a schematic view illustrating an alternative method for finding the value(s) of the one or more parameters of the diffracting structure. Instead of constructing a multi-dimensional look-up-table of high resolution, a coarse library 102 may first be constructed as described above. The measured data 106 as shown in FIG. 2 is then matched against the spectra in the coarse library 102 to find the best fit 108. This is shown schematically in FIG. 3 as one of the sites. In some situations, there may be more than one spectra that fit the measured data 106, in which case there would be multiple sites, such as n sites shown in FIG. 3 where n is a positive integer. Then a small fine local library or look-up-table may be constructed for each site where the parameters are allowed to vary over a small range in the neighborhood of each site. The measured data is then compared to the spectra in the small fine local library to find the best match.

Any standard search algorithm, such as, for example, bi-section, can be applied to each local box to make local matching even more efficient. In such cases, not all the points of the local box are pre-calculated, only the points along the searching path are calculated, which reduces the amount of computing.

Applicants have found that the measured data, such as diffraction intensities or changes in polarization state, are more sensitive at certain wavelengths of the radiation compared to others as shown in FIG. 4. Noise in the system, such as that in system 10 shown in FIG. 1A, may also be a function of wavelengths, also illustrated in FIG. 4. Therefore, it will be desirable to operate the above-described process or method using data at wavelengths where the diffraction intensity or change in polarization state is the most sensitive. It may also be desirable to operate the above-described process or method using data at wavelengths where the system noise is low or at a minimum. In the example shown in FIG. 4, one would, therefore, choose to measure and calculate using a model diffraction data at wavelengths in the neighborhood of 410, 525 or 570 nm but would avoid diffraction intensity data above 580 nm.

In the analysis of two-dimensional diffraction gratings, it is conventional to employ a stack of lamellar grating layers to approximate an arbitrary profile. See, for example, the article "Multilayer Model Method for Diffraction Gratings of Arbitrary Profile, Depth, and Permativity," by Liefeng Li, *J. Opt. Soc. Am. A.*, Vol. 10, No. 12, December 1993, pages 2581-2591. The interaction between a beam of electromagnetic radiation and the grating is modeled using methods such as a multi-modal method or a rigorous coupled-wave analysis method. These methods involve the calculation of eigenvalues. However, in all of the methods proposed before this invention, the eigenvalues are calculated from scratch each time the parameters of a grating are to be determined. Since the calculation of eigenvalues is time consuming and cumbersome, the methods proposed are likewise cumbersome and time consuming.

Another aspect of the invention is based on the recognition that frequently different diffraction gratings measured may differ in only certain respects so that the data such as eigenvalues obtained with respect to portions of the gratings that are the same may be stored for future reference and reused, thereby saving time and effort in the calculation.

A look-up-table of the eigenvalues may also be pre-computed, so that any eigenvalue within a certain range may be calculated with interpolation from the eigenvalue look-up-table. Any of standard interpolation routines, such as linear, or cubic splines, may be used for eigenvalues interpolation. This will make the calculation of eigenvalues easier, faster, and more reliable.

The algorithms, including storing and subsequent re-use, and the other algorithms, including pre-computing look-up-table and subsequent interpolation, may be used also for S-matrices, as described below.

This is illustrated in FIGS. 5 and 6. In reference to FIGS. 1B and 5, S-matrix propagation is first performed in the bottom film stack 16c (block 150). Then the grating S-matrix is calculated using a multi-layer model containing a stack or pile of slabs. This is shown more clearly in FIG. 6. As shown in FIG. 6, the left side 160 of a portion of a grating line in FIG. 1B is approximated in shape by four slabs, 162a, 162b, 162c and 162d. The S-matrix is calculated for each of the four slabs. Then the total grating S-matrix (block 152) is calculated from the S-matrices for the slabs. Then the S-matrix is found for the top film stack 16a (block 154).

One aspect of the invention is based on Applicants' observation that for a number of different diffraction gratings that are modeled to create a look-up-table, even though their profiles differ, the bottom portions of the gratings still may be essentially the same. In such circumstances, the S-matrix values of the bottom slabs in the stack or pile 162 may be the same for all the gratings, even though the top number of slabs may differ. In such circumstances, it may be useful to store the S-matrix values for all the slabs after they have been calculated for one diffracting grating, so that the S-matrix data for the slabs used to model another different grating structure can be re-used and do not have to be recalculated. This saves time and effort. Thus, as shown in FIG. 6, after the grating structure with the left side 160 has been modified, a different structure is to be modeled, and another different multi-layer model is constructed with slabs. It may happen that the bottom two slabs for this different grating structure turn out to be the same as slabs 162a, 162b for side 160, whereas the top number of slabs are different from slabs 162c and 162d. In such circumstances, the S-matrix values for slabs 162a, 162b already obtained in the modeling of the grating with left side 160 may be reused for the other different structure.

Thus as noted above, it would be useful to store the values of the S-matrix of one or more of the slabs at or near the bottom of the pile 162. Where the new structure whose parameters are of interest differ from the one already modeled only in some of the slabs at the top, all one needs to do is alter the dimensions of one or more slabs at the top of the pile 162 to approximate such other new and different grating structure and reuse the stored S-matrices of some of the slabs at or near the bottom of the pile for obtaining the value(s) of the one or more parameters of the other diffracting structure.

While the diffracting structure may comprise a single material, it is also possible for the structure to comprise layers of different material. The above-described multi-layer model accounts for the same or different kinds of materials in the structure. The manner in which the materials are taken into account is known to those skilled in the art and will not be described here.

Where the model employed is a rigorous coupled-wave analysis model, the model also calculates eigenfunctions. The eigenfunctions may also be stored in addition to the eigenvalues for use in the modeling and analysis of other diffracting structures.

In addition to modeling the pile of slabs 162, the model employed may also include the propagation of S-matrices through the bottom film stack (block 150) and through the top film stack (block 154). Where other different diffracting structures to be modeled are situated over similar bottom film stacks 16c or underneath similar top film stacks 16a, the values of such S-matrices for the film stacks may be reused in the measurement of such other different grating structure, so that these matrices do not have to be recalculated. This saves time and effort. Therefore, according to another aspect of the invention, the values of the S-matrices for the bottom and top film stacks are also stored for use in finding the value(s) of the one or more parameters of a different diffracting structure associated with similar bottom and top film stacks. Obviously, the S-matrices for the top and bottom film stacks may be used independently of one another so that the calculation for another diffracting structure may involve only the top or bottom film stack S-matrices, but not both.

As shown in FIG. 1B, a grating structure 16b may be situated under or over film stacks. In some semiconductor wafers, these film stacks may vary in their optical characteristics across the wafer or between different wafers that have the same diffraction grating. In such circumstances, it may be desirable to process only data obtained at wavelengths that are less sensitive to these variations in optical characteristics of the film stacks. In this manner, the effect of the variations on the calculations would be less pronounced, which would simplify the calculations. This is illustrated, for example, in FIG. 7 which is a graphical plot of the skin depth of polysilicon versus wavelength. As shown in FIG. 7, polysilicon is substantially opaque at wavelengths from the ultraviolet range to about 380 nm. Therefore, if the intensity or change in polarization state data that are analyzed are only those for this wavelength range, the effect of variations in optical characteristics of the top or bottom film stacks on the measurements can be essentially ignored.

Even if the underlying film is not opaque, its influence on the reflectance from the whole structure my be negligible at certain wavelengths due to multi-layer interference. For these wavelengths the spectrum is insensitive to film stack fluctuations, yet remains sensitive to grating parameters. Therefore, we can use reflectance at these wavelengths to measure the grating parameters, while ignoring fluctuations in film stacks.

The intensity or change in polarization state data may be more sensitive as a function of wavelength to the change in the value(s) of the one or more parameters at certain wavelengths than at other wavelengths. Another aspect of the invention is based on the observation that by increasing the density of data points of the intensity or change in the polarization state data at wavelengths where the data exhibit sharp peaks or valleys as a function of wavelength, the spectral signature indicated by the resulting data points may be more accurate. This is illustrated in FIG. 8 which is a graphical plot of diffraction intensity versus wavelength of a particular diffraction structure. Thus, as can be seen from FIG. 8, the change in the diffraction intensity versus wavelength is rather smooth at certain wavelengths, such as for wavelengths within the regions 182 and 188. There are, however, other regions in which the diffraction intensity changes rapidly with a small change in wavelength, such as within regions 184 and 186; within such regions, it would be desirable to increase the density of data samples to more accurately represent the shape of the curve, which would yield more accurate results in subsequent processing and curve fitting or data matching.

Three-Dimensional Grating

In semiconductor fabrication, three-dimensional diffracting structures are sometimes encountered, where the structure comprises a two-dimensional layout of hills on top of an underlying film stack (it may also be underneath a top film stack). Structure 200 illustrates one period of the grating.

To model the three-dimensional grating of which structure 200 is a part, a pseudo-periodic solution in the grating is to be found which matches with plane waves outside the grating comprising incident and reflected waves. To obtain the solution, the three-dimensional structure 200 within one period is considered. In this way, the entire structure 200 is approximated with a pile of cylinders.

A solution for each slab is first found, where the solution is a product of a vertically propagating plane wave times the horizontal two-dimensional solution of the pseudo-periodic boundary-value problem in the cross-section plane, where the boundary conditions both in the x and y directions are shown in FIG. 10 and are set forth below as well:

$$E(x, y_{m+1}) = E(x, y_0) e^{ik_0 y d_y} \quad (2)$$

As noted from FIG. 9, conical structure 200 is situated on a reference plane 202. A model of structure 200 is provided by cutting a three-dimensional contour resembling a representative portion such as structure 200 of the three-dimensional grating along planes parallel to plane 202 to obtain a number of slices such as slice 200(i) with i ranging from 1 to m, where m is a positive integer. Then each slice is approximated in shape by a cylindrical slab to arrive at structure 200', where the modeling is illustrated schematically by arrow 204 in FIG. 9. For purposes of illustration, only five cylinders are illustrated in structure 200'. Where structure 200 is not conical in shape, the five slabs 200'(1), . . . 200'(5) will not be circular cylinders but can take on other shapes in their cross-section, such as ellipses or other shapes. In general, structure 200 may be approximated by a contour 200' comprising a pile of a plurality of slabs, where each slab may take on the shape of a circular cylinder, elliptical cylinder or other suitable shapes. For each slab 200'(i) in contour 200', i ranging from 1 to m, an array of rectangular blocks is constructed to approximate the shape of the slab as illustrated in FIG. 10. As shown in FIG. 10, a particular slab which is substantially ellptical in shape is approximated (arrow 224) by an array of five rectangular blocks 210, 212, 214, 216 and 218.

As described above, to obtain the two-dimensional solution, each slab such as 200'(i) is approximated by an array of rectangular blocks. In the embodiment of FIG. 10, slab 200'(i) is approximated by five rectangular blocks 210-218. A one-dimensional boundary value problem for each of the five blocks 210-218 is found in a manner known to those skilled in the art. The one-dimensional solutions for neighboring blocks 210-218 are then matched to construct a two-dimensional solution for slab 200'(i) which is a product of one-dimensional solutions of the rectangular blocks and a plane wave propagating in the y direction with the wave number $k_y$. The right value of $k_y$ is then searched to make the two-dimensional solution meet pseudo-periodic boundary conditions in the y direction. The two-dimensional solution found in this manner is a two-dimensional eigenfunction. The two-dimensional solutions found for each of the slabs is then matched with the plane waves outside the contour 200' to construct a three-dimensional solution for the contour 200'. The three dimensional solution for the whole grating is then found which provides the diffraction efficiencies both for the reflected and transmitted waves. This three-dimensional solution may be stored in a database and be provided as a datasource useful for finding a value related to one or more parameters of a three-dimensional diffracting structure.

FIG. 11 is a perspective view of a two-dimensional grating relative to a plane of incidence of a measurement beam to illustrate a system for measuring line roughness. Because of the way semiconductor wafers are processed, sometimes line roughness on the wafer surface may result from the manufacturing processes. The line roughness is deviation of the two-dimensional grating from straight line shape. Another aspect of the invention is based on the observation that by measuring the effects of the lines on polarization of reflected light, a measure of the line roughness can be obtained. This is illustrated in FIG. 11. A wafer surface 300 has thereon an array of two-dimensional gratings 302, which is shown schematically to illustrate the concept. A beam 304 of radiation is incident on the grating 302 in the plane of incidence 306 which is preferably, substantially orthogonal to the grating lines 302. Beam 304 is polarized and has a known polarization state. Light that is diffracted by grating 302 is then detected using the spectroscopic ellipsometer 34 as described above or any other suitable instrument (for example, a polarizer combined with a spectrometer) to measure the change in polarization state of the beam 304 caused by grating 302. The change in polarization state so measured may indicate characteristics of the grating 302.

In one embodiment, beam 304 is linearly polarized in a direction in the plane of incidence 306 (P-polarization) or in a direction substantially normal to plane 306 (S-polarization). The spectroscopic ellipsometer 34 is then used to measure the cross-polarization coefficient as a measure of the line roughness. In other words, if beam 304 is S-polarized, the spectroscopic ellipsometer would measure the intensity of P-polarization components of the reflected radiation where the ratio of the P-polarization components to the intensity of the illumination beam 304 would give the cross-polarization coefficient. If beam 304 is P-polarized, the spectroscopic ellipsometer would measure the intensity of S-polarization components of the reflected radiation where the ratio of the S-polarization components to the intensity of the illumination beam 304 would give the cross-polarization coefficient. If there is no line roughness, this coefficients would be zero.

FIG. 12 is a block diagram of an integrated scatterometer, a photolithographic stepper and an etcher to illustrate another aspect of the invention. A layer of material such as photoresist is formed on the surface of a semiconductor wafer by means of stepper 350, where the photoresist forms a grating structure on the wafer. One or more of the CD, H, SWA and other parameters of the grating structure are then measured using system 10 of FIG. 1A and one or more of the above-described techniques may be employed if desired to find the value(s) of the one or more parameters of the photoresist pattern. Such value(s) from the computer 40 are then fed back to stepper 350, where such information may be used to alter the lithographic process in stepper 350 to correct any errors. In semiconductor processing, after a layer of photoresist has been formed on the wafer, an etching process may be performed, such as by means of etcher 360. The layer of photoresist is then removed in a manner known in the art and the resulting grating structure made of semiconductor material on the wafer may again be measured if desired using system 10. The value(s) measured using any one or more of the above-described techniques may be supplied to the etcher for altering any one of the etching parameters in order to correct any errors that have been found using system 10. Of course the results obtained by one or more of the above described techniques in system 10 may be used in both the stepper and the etcher, or in either the stepper or the etcher but not both. The stepper 350 and/or etcher 360 may form an integrated single tool with the system 10 for finding the one or more parameters of a diffracting structure, or may be separate instruments from it.

Software Upgrades

The invention has been described above, employing a system such as that shown in FIG. 1A. While the various optical components in the system of FIG. 1A are used to obtain measured data from the sample, many of the other processes are performed by computer 40. Thus, for many systems currently being used by manufacturers such as semiconductor manufacturers, the computers used in the systems may not have the capability to perform the techniques described above. Thus, another aspect of the invention envisions that the software in these computers can be upgraded so that computer 40 can perform one or more of the above described different functions. Therefore, another aspect of the invention involves the software components that are loaded to computer 40 to perform the above-described functions. These functions, in conjunction with the optical components of system 10 in FIG. 1A, provide results with the different advantages outlined above. The software or program components may be installed in computer 40 in a variety of ways.

As will be understood in the art, the inventive software components may be embodied in a fixed media program component containing logic instructions and/or data that when loaded into an appropriately configured computing device to cause that device to perform according to the invention. As will be understood in the art, a fixed media program may be delivered to a user on a fixed media for loading in a users computer or a fixed media program can reside on a remote server that a user accesses through a communication medium in order to download a program component. Thus another aspect of the invention involves transmitting, or causing to be transmitted, the program component to a user where the component, when downloaded into the user's device, can perform any one or more of the functions described above.

FIG. 13 shows an information appliance (or digital device) that may be understood as a logical apparatus that can read instructions from media 417 and/or network port 419. Apparatus 40 can thereafter use those instructions to direct server or client logic, as understood in the art, to embody aspects of the invention. One type of logical apparatus that may embody the invention is a computer system as illustrated in 40, containing CPU 404, optional input devices 409 and 411, disk drives 415 and optional monitor 405. Fixed media 417 may be used to program such a system and may represent a disk-type optical or magnetic media, magnetic tape, solid state memory, etc. One or more aspects of the invention may be embodied in whole or in part as software recorded on this fixed media. Communication port 419 may also be used to initially receive instructions that are used to program such a system to perform any one or more of the above-described functions and may represent any type of communication connection, such as to the internet or any other computer network. The instructions or program may be transmitted directly to a user's device or be placed on a network, such as a website of the internet to be accessible through a user's device. All such methods of making the program or software component available to users are known to those in the art and will not be described here.

The invention also may be embodied in whole or in part within the circuitry of an application specific integrated circuit (ASIC) or a programmable logic device (PLD). In such a case, the invention may be embodied in a computer understandable descriptor language which may be used to create an ASIC or PLD that operates as herein described.

While the invention has been described above by reference to various embodiments, it will be understood that changes and modifications may be made without departing from the scope of the invention, which is to be defined only by the appended claims and their equivalents. All references mentioned herein are incorporated in their entirety.

What is claimed is:

1. An apparatus for finding a value of one or more parameters of a diffracting structure wherein a measurement is carried out by directing a polychromatic beam of electromagnetic radiation at said diffracting structure and detecting corresponding intensities of a diffraction of said beam at a number of wavelengths from said structure, comprising:

a system carrying out a measurement of the structure to obtain measured intensities of a diffraction from the structure; and a processor providing a set of intensity data of the diffraction at the wavelengths corresponding to a first set of values of said one or more parameters, and performing an optimized estimation within a neighborhood of the set of intensity data using said measured intensities to arrive at a second set of values of the one or more parameters; wherein said processor generates a library of sets of intensity data of the diffraction at the wavelengths, wherein each set of data is generated assuming a corresponding set of values of the one or more parameters, said sets of values of the one or more parameters covering expected ranges of the one or more parameters; and wherein said processor compares the measured intensities to the sets of intensity data to find the set of intensity data that corresponds to the first set of values of said one or more parameters.

2. An apparatus for detecting line roughness of a surface having grating lines thereon, comprising:

optics illuminating the surface with radiation in an incidence plane substantially normal to the grating lines, said radiation having only S or P polarization components;

a detector detecting radiation reflected by the surface; and a processor determining cross-polarization coefficient of the radiation reflected by the surface as an indication of surface line roughness.

3. A computer readable storage device embodying a program of instructions executable by a computer to perform a method for finding a value of one or more parameters of a diffracting structure wherein a measurement is carried out by directing a polychromatic beam of electromagnetic radiation at said diffracting structure and detecting corresponding intensities of a diffraction of said beam at a number of wavelengths from said structure to obtain measured intensities of the diffraction from the structure; sad method comprising:

providing a set of intensity data of the diffraction at the wavelengths corresponding to a first set of values of said one or more parameters; and performing an optimized estimation within a neighborhood of the set of intensity data using said measured intensities to arrive at a second set of values of the one or more parameters; wherein said providing includes:

generating a library of sets of intensity data of the diffraction at the wavelengths, wherein each set of data is generated assuming a corresponding set of values of the one or more parameters, said sets of values of the one or more parameters covering expected ranges of the one or more parameters; and comparing the measured intensities to the sets of data to find the set of intensity data that corresponds to the first set of values of said one or more parameters.

4. A method for transmitting a program of instructions executable by a computer to perform a process for finding a value of one or more parameters of a diffracting structure wherein a measurement is carried out by directing a polychromatic beam of electromagnetic radiation at said diffracting structure and detecting corresponding intensities of a diffraction of said beam at a number of wavelengths from said structure to obtain measured intensities of the diffraction from the structure; said method comprising:

causing a program of instructions to be transmitted to a client device, thereby enabling the client device to perform, by means of such program, the following process:

providing a set of intensity data of the diffraction at the wavelengths corresponding to a first set of values of said one or more parameters; and performing an optimized estimation within a neighborhood of the set of intensity data using said measured intensities to arrive at a second set of values of the one or more parameters; wherein said providing includes:

generating a library of sets of intensity data of the diffraction at the wavelengths, wherein each set of data is generated assuming a corresponding set of values of the one or more parameters, said sets of values of the one or more parameters covering expected ranges of the one or more parameters;

comparing the measured intensities to the sets of data to find the set of intensity data that corresponds to the first set of values of said one or more parameters; and supplying the second set of values of the one or more parameters to a processing machine to compensate for any errors in the one or more parameters during processing by the machine.

5. A method for finding a value of one or more parameters of a diffracting structure wherein a measurement is carried out by directing a polychromatic beam of electromagnetic radiation at said diffracting structure and detecting corresponding intensities of a diffraction of said beam at a number of wavelengths from said structure, comprising:

measuring intensities of a diffraction from the structure;

providing a set of intensity data of the diffraction at the wavelengths corresponding to a first set of values of said one or more parameters; and performing an optimized estimation within a neighborhood of the set of intensity data using said measured intensities to arrive at a second set of values of the one or more parameters;

wherein said providing comprises:

generating a library of sets of intensity data of the diffraction at the wavelengths, wherein each set of data is generated assuming a corresponding set of values of the one or more parameters, said sets of values of the one or more parameters covering expected ranges of the one or more parameters;

comparing the measured intensities to the sets of data to find the set of intensity data that corresponds to the first set of values of said one or more parameters; and supplying the second set of values of the one or more parameters to a processing machine to compensate for any errors in the one or more parameters during processing by the machine.

6. An apparatus for finding a value of one or more parameters of a diffracting structure wherein a measurement is carried out by directing a polychromatic beam of electromagnetic radiation at said diffracting structure and detecting corresponding intensities of a diffraction of said beam at a number of wavelengths from said structure, comprising:

a system carrying out a measurement of the structure to obtain measured intensities of a diffraction from the structure; and a processor selecting at least one first set of values of said one or more parameters from a plurality of sets of such values using the measured intensities of a diffraction from the structure, providing at least one set of intensity data of the diffraction at the wavelengths corresponding to the at least one first set of values of said one or more parameters, and performing an optimized estimation within a neighborhood of the at least one set of intensity data using said measured intensities to arrive at a second set of values of the one or more parameters.

7. The apparatus of claim 6, wherein said processor generates a library of sets of intensity data of the diffraction at the wavelengths, wherein each set of data is generated assuming a corresponding set of values of the one or more parameters among the plurality of sets, said plurality of sets of values of the one or more parameters covering expected ranges of the one or more parameters; and wherein said processor compares the measured intensities to the sets of data in the library to find the set of intensity data that corresponds to the at least one first set of values of said one or more parameters.

8. The apparatus of claim 6, wherein said processor selects more than one set of values of said one or more parameters from the plurality of sets of such values using the measured intensities of a diffraction from the structure, provides one set of intensity data of the diffraction at the wavelengths corresponding to each of the more than one set of values of said one or more parameters, and performs optimized estimation within a neighborhood of each of the sets of intensity data so provided using said measured intensities to arrive at a second set of values of the one or more parameters.

9. The apparatus of claim 8, wherein the processor computes only at points along a search path in the neighborhood of each of the sets of intensity data so provided, without also computing at other points in such neighborhoods.

10. A method for finding a value of one or more parameters of a diffracting structure wherein a measurement is carried out by directing a polychromatic beam of electromagnetic radiation at said diffracting structure and detecting corresponding intensities of a diffraction of said beam at a number of wavelengths from said structure, comprising:

measuring intensities of a diffraction from the structure; and selecting at least one first set of values of said one or more parameters from a plurality of sets of such values using the measured intensities of a diffraction from the structure;

providing at least one set of intensity data of the diffraction at the wavelengths corresponding to the at least one first set of values of said one or more parameters;

performing an optimized estimation within a neighborhood of the at least one set of intensity data using said measured intensities to arrive at a second set of values of the one or more parameters; and supplying the second set of values of the one or more parameters to a processing machine to compensate for any errors in the one or more parameters during processing by the machine.

11. The method of claim 10, further comprising:
generating a library of sets of intensity data of the diffraction at the wavelengths, wherein each set of data is generated assuming a corresponding set of values of the one or more parameters among the plurality of sets, said plurality of sets of values of the one or more parameters covering expected ranges of the one or more parameters; and
comparing the measured intensities to the sets of data in the library to find the set of intensity data that corresponds to the at least one first set of values of said one or more parameters.

12. The method of claim 11, wherein said selecting selects more than one set of values of said one or more parameters from the plurality of sets of such values using the measured intensities of a diffraction from the structure, said providing provides one set of intensity data of the diffraction at the wavelengths corresponding to each of the more than one set of values of said one or more parameters, and said performing performs optimized estimation within a neighborhood of each of the sets of intensity data so provided using said measured intensities to arrive at a second set of values of the one or more parameters.

13. The apparatus of claim 12, wherein only values at points along a search path in the neighborhood of each of the sets of intensity data so provided are computed, without also computing at other points in such neighborhoods in the optimized estimation.

14. An apparatus for finding a value of one or more parameters of a diffracting structure wherein a measurement is carried out by directing a polychromatic beam of electromagnetic radiation at said diffracting structure and detecting corresponding changes in polarization state of a diffraction of said beam at a number of wavelengths from said structure, comprising:
a system carrying out a measurement of the structure to obtain measured changes in polarization state of a diffraction from the structure; and
a processor providing a set of change in polarization state data of the diffraction at the wavelengths corresponding to a first set of values of said one or more parameters, and performing an optimized estimation within a neighborhood of the set of change in polarization state data using said measured changes in polarization state to arrive at a second set of values of the one or more parameters; wherein said processor generates a library of sets of change in polarization state data of the diffraction at the wavelengths, wherein each set of data is generated assuming a corresponding set of values of the one or more parameters, said sets of values of the one or more parameters covering expected ranges of the one or more parameters; and wherein said processor compares the measured changes in polarization state to the sets of data to find the set of change in polarization state data that corresponds to the first set of values of said one or more parameters.

15. A computer readable storage device embodying a program of instructions executable by a computer to perform a method for finding a value of one or more parameters of a diffracting structure wherein a measurement is carried out by directing a polychromatic beam of electromagnetic radiation at said diffracting structure and detecting corresponding changes in polarization state of a diffraction of said beam at a number of wavelengths from said structure to obtain measured changes in polarization state of the diffraction from the structure; sad method comprising:
providing a set of change in polarization state data of the diffraction at the wavelengths corresponding to a first set of values of said one or more parameters; and
performing an optimized estimation within a neighborhood of the set of change in polarization state data using said measured changes in polarization state to arrive at a second set of values of the one or more parameters; wherein said providing includes:
generating a library of sets of change in polarization state data of the diffraction at the wavelengths, wherein each set of data is generated assuming a corresponding set of values of the one or more parameters, said sets of values of the one or more parameters covering expected ranges of the one or more parameters; and
comparing the measured changes in polarization state to the sets of data to find the set of change in polarization state data that corresponds to the first set of values of said one or more parameters.

16. A method for transmitting a program of instructions executable by a computer to perform a process for finding a value of one or more parameters of a diffracting structure wherein a measurement is carried out by directing a polychromatic beam of electromagnetic radiation at said diffracting structure and detecting corresponding changes in polarization state of a diffraction of said beam at a number of wavelengths from said structure to obtain measured changes in polarization state of the diffraction from the structure; said method comprising:
causing a program of instructions to be transmitted to a client device, thereby enabling the client device to perform, by means of such program, the following process:
providing a set of change in polarization state data of the diffraction at the wavelengths corresponding to a first set of values of said one or more parameters; and
performing an optimized estimation within a neighborhood of the set of change in polarization state data using said measured changes in polarization state to arrive at a second set of values of the one or more parameters; wherein said providing includes:
generating a library of sets of change in polarization state data of the diffraction at the wavelengths, wherein each set of data is generated assuming a corresponding set of values of the one or more parameters, said sets of values of the one or more parameters covering expected ranges of the one or more parameters;
comparing the measured changes in polarization state to the sets of data to find the set of change in polarization state data that corresponds to the first set of values of said one or more parameters; and
supplying the second set of values of the one or more parameters to a processing machine to compensate for any errors in the one or more parameters during processing by the machine.

17. A method for finding a value of one or more parameters of a diffracting structure wherein a measurement is carried out by directing a polychromatic beam of electromagnetic radiation at said diffracting structure and detecting corresponding changes in polarization state of a diffraction of said beam at a number of wavelengths from said structure, comprising:
measuring changes in polarization state of a diffraction from the structure;

providing a set of change in polarization state data of the diffraction at the wavelengths corresponding to a first set of values of said one or more parameters; and performing an optimized estimation within a neighborhood of the set of change in polarization state data using said measured changes in polarization state to arrive at a second set of values of the one or more parameters;

wherein said providing comprises:

generating a library of sets of change in polarization state data of the diffraction at the wavelengths, wherein each set of data is generated assuming a corresponding set of values of the one or more parameters, said sets of values of the one or more parameters covering expected ranges of the one or more parameters;

comparing the measured changes in polarization state to the sets of data to find the set of change in polarization state data that corresponds to the first set of values of said one or more parameters; and supplying the second set of values of the one or more parameters to a processing machine to compensate for any errors in the one or more parameters during processing by the machine.

18. An apparatus for finding a value of one or more parameters of a diffracting structure wherein a measurement is carried out by directing a polychromatic beam of electromagnetic radiation at said diffracting structure and detecting corresponding changes in polarization state of a diffraction of said beam at a number of wavelengths from said structure, comprising:

a system carrying out a measurement of the structure to obtain measured changes in polarization state of a diffraction from the structure; and a processor selecting at least one first set of values of said one or more parameters from a plurality of sets of such values using the measured changes in polarization state of a diffraction from the structure, providing at least one set of change in polarization state data of the diffraction at the wavelengths corresponding to the at least one first set of values of said one or more parameters, and performing an optimized estimation within a neighborhood of the at least one set of change in polarization state data using said measured changes in polarization state to arrive at a second set of values of the one or more parameters.

19. The apparatus of claim 18, wherein said processor generates a library of sets of change in polarization state data of the diffraction at the wavelengths, wherein each set of data is generated assuming a corresponding set of values of the one or more parameters among the plurality of sets, said plurality of sets of values of the one or more parameters covering expected ranges of the one or more parameters; and wherein said processor compares the measured changes in polarization state to the sets of data in the library to find the set of change in polarization state data that corresponds to the at least one first set of values of said one or more parameters.

20. The apparatus of claim 18, wherein said processor selects more than one set of values of said one or more parameters from the plurality of sets of such values using the measured changes in polarization state of a diffraction from the structure, provides one set of change in polarization state data of the diffraction at the wavelengths corresponding to each of the more than one set of values of said one or more parameters, and performs optimized estimation within a neighborhood of each of the sets of change in polarization state data so provided using said measured changes in polarization state to arrive at a second set of values of the one or more parameters.

21. The apparatus of claim 20, wherein the processor computes only at points along a search path in the neighborhood of each of the sets of change in polarization state data so provided, without also computing at other points in such neighborhoods.

22. A method for finding a value of one or more parameters of a diffracting structure wherein a measurement is carried out by directing a polychromatic beam of electromagnetic radiation at said diffracting structure and detecting corresponding changes in polarization state of a diffraction of said beam at a number of wavelengths from said structure, comprising:

measuring changes in polarization state of a diffraction from the structure; and selecting at least one first set of values of said one or more parameters from a plurality of sets of such values using the measured changes in polarization state of a diffraction from the structure;

providing at least one set of change in polarization state data of the diffraction at the wavelengths corresponding to the at least one first set of values of said one or more parameters;

performing an optimized estimation within a neighborhood of the at least one set of change in polarization state data using said measured changes in polarization state to arrive at a second set of values of the one or more parameters; and supplying the second set of values of the one or more parameters to a processing machine to compensate for any errors in the one or more parameters during processing by the machine.

23. The method of claim 22, further comprising:

generating a library of sets of change in polarization state data of the diffraction at the wavelengths, wherein each set of data is generated assuming a corresponding set of values of the one or more parameters among the plurality of sets, said plurality of sets of values of the one or more parameters covering expected ranges of the one or more parameters; and comparing the measured changes in polarization state to the sets of data in the library to find the set of change in polarization state data that corresponds to the at least one first set of values of said one or more parameters.

24. The method of claim 23, wherein said selecting selects more than one set of values of said one or more parameters from the plurality of sets of such values using the measured changes in polarization state of a diffraction from the structure, said providing provides one set of change in polarization state data of the diffraction at the wavelengths corresponding to each of the more than one set of values of said one or more parameters, and said performing performs optimized estimation within a neighborhood of each of the sets of change in polarization state data so provided using said measured changes in polarization state to arrive at a second set of values of the one or more parameters.

25. The apparatus of claim 24, wherein only values at points along a search path in the neighborhood of each of the sets of change in polarization state data so provided are computed, without also computing at other points in such neighborhoods in the optimized estimation.

* * * * *